US010087495B2

United States Patent
Matheny et al.

(10) Patent No.: US 10,087,495 B2
(45) Date of Patent: *Oct. 2, 2018

(54) BACILLUS STRAINS AND COMPOSITIONS

(71) Applicant: Envera, LLC, West Chester, PA (US)

(72) Inventors: Michael Matheny, Landenberg, PA (US); Zivile Panaviene, Wayne, PA (US)

(73) Assignee: Envera, LLC, West Chester, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/202,693

(22) Filed: Jul. 6, 2016

(65) Prior Publication Data

US 2016/0312316 A1    Oct. 27, 2016

Related U.S. Application Data

(62) Division of application No. 14/254,937, filed on Apr. 17, 2014, now Pat. No. 9,410,213.

(60) Provisional application No. 61/854,062, filed on Apr. 17, 2013.

(51) Int. Cl.
| | | |
|---|---|---|
| *A01N 63/00* | (2006.01) | |
| *C12R 1/07* | (2006.01) | |
| *C02F 3/34* | (2006.01) | |
| *A01N 63/04* | (2006.01) | |
| *C12N 1/20* | (2006.01) | |

(52) U.S. Cl.
CPC .............. *C12R 1/07* (2013.01); *A01N 63/00* (2013.01); *A01N 63/04* (2013.01); *C02F 3/34* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 6,524,842 B1 | 2/2003 | Vainberg et al. | |
| 6,524,998 B1 * | 2/2003 | Kloepper ............... | A01N 63/00 504/100 |
| 2009/0260107 A1 | 10/2009 | English et al. | |
| 2012/0149571 A1 * | 6/2012 | Kloepper ............... | A01N 63/00 504/117 |

FOREIGN PATENT DOCUMENTS

| | | |
|---|---|---|
| JP | 2012-16320 | 1/2012 |
| WO | 2011140051 | 11/2011 |

OTHER PUBLICATIONS

Karthiba et al. "PGPR and entomopathogenic fungus bioformulation for the synchronous management of leaffolder pest and sheath blight disease of rice" Pest Manag Sci 2010; 66: 555-564 (Year: 2010).*
Gutierrez-Luna, Francisca M., et al., "Plant Growth-Promoting Rhizobacteria Modulate Root-System Architecture in Arabidopsis Thaliana Through Volatile Organic Compound Emission" May 2010, Symbiosis, vol. 51, No. 1, pp. 75-83.

Erturk, Y, et al., "Yield and Growth Response of Strawberry to Plant Growth-Promoting Rhizobacteria Inoculation", Apr. 3, 2012, Journal of Plant Nutrition, vol. 35, No. 6, pp. 817-826.
Purswani, Jessica, et al., "Selection and Identification of Bacterial Stains with Methyl-tert-Butyl Ether, Ethyl-tert-Butyl Ether, and tert-Amyl Methyl Ether Degrading Capacities", Nov. 1, 2006, Environmental Toxicology and Chemistry, vol. 27, No. 11, pp. 2296-2303.
Munoz, Ana, et al., "Biodegradation and Mineralization of Metolachlor and Alachlor by Candida Xestobii" Jan. 26, 2011, Journal of Agricultural and Food Chemistry, vol. 59, No. 5, pp. 619-627.
Yang, Chunyu, et al., "Metabolic Versatility of Halotolerant and Alkaliphilic Strains of Halomonas Isolated from Alkaline Black Liquor", Sep. 1, 2010, Bioresource Technology, vol. 101, No. 17, pp. 6778-6784.
Hatzinger, Paul B., et al., "Biodegradation of Methyl tert-Butyl Ether by a Pure Bacterial Culture", Dec. 1, 2001, Applied and Environmental Microbiology, vol. 67, No. 12, pp. 5601-5607.
Supplementary European Search Report in co-pending European Patent Application No. 14785033, dated Oct. 26, 2016, 9 Pages.
Heyrman et al., "Study of Mural Painting Isolates, Leading to the Transfer of 'Bacillus maroccanus' and 'Bacillus carotarum' to Bacillus simplex, emended description of Bacillus simplex, re-examination of the strains previously attributed to 'Bacillus macroides' and Description of Bacillus muralis", International Journal of Systematic and Evolutionary Microbiology, 2005, vol. 55, pp. 119-131.
Gomaa et al., "16S rRNA Characterization of a Bacillus Isolate and its Tolerance Profile After Subsequent Subculturing", Arab J. Biotech., 2007, vol. 10, No. 1, pp. 107-116.
Kuisiene et al., "Bacillus butanolivorans sp. nov., a species with industrial application for the remediation of n-butanol", International Journal of Systematic and Evolutionary Microbiology, 2008, vol. 58, pp. 505-509.
"Evaluation of Application of Microbial Solidification in Coastal Zone using Microorganisms with Urease Activity", Japanese Geotechnical Journal, 2011, vol. 6, No. 2, pp. 305-3015.
Kwon, Soon-Wo, et al., "Sporosarcina koreenis sp. nov. and Sporosarcina soli sp. nov., Isolated from Soil in Korea", International Journal of Systematic and Evolutionary Microbiology, 2007, vol. 57, pp. 1694-1698.
Japanese Office Action dated Mar. 6, 2018, relating to Japanese co-pending application No. 2016-509092—6 Pages (with English Translation—6 Pages).

* cited by examiner

*Primary Examiner* — Thane E Underdahl
(74) *Attorney, Agent, or Firm* — McCarter & English, LLP

(57) ABSTRACT

In one aspect, the present invention relates to novel *Bacillus* strains ENV 734 (NRRL B-50800), ENV 735 (NRRL B-50801), ENV 736 (NRRL B-50802), and ENV 737 (NRRL B-50803). These strains possess a high degree of homology with both *Bacillus simplex* and *Bacillus butanolivorans*, but unexpectedly exhibit desirable high salt tolerance as well as low temperature growth and urease production. In another aspect, the present invention relates to compositions comprising at least one of such strains and an acceptable carrier, and methods of preparing the compositions. Such compositions are suitable for use in industrial, agricultural, aquacultural, environmental, wastewater treatment and/or probiotic applications. Methods for enhancing the growth of a plant propagative material and methods for treating wastewater are also provided.

20 Claims, No Drawings

BACILLUS STRAINS AND COMPOSITIONS

CROSS REFERENCE TO RELATED APPLICATIONS

This application is a Divisional of U.S. application Ser. No. 14/254,937, filed Apr. 17, 2014, which claims priority to U.S. Provisional Application Ser. No. 61/854,062 filed Apr. 17, 2013, each of which is hereby incorporated by reference in its entirety.

FIELD OF THE INVENTION

In one aspect, the present invention relates to novel *Bacillus* strains ENV 734 (NRRL B-50800), ENV 735 (NRRL B-50801), ENV 736 (NRRL B-50802), and ENV 737 (NRRL B-50803). These strains possess a high degree of homology with both *Bacillus simplex* and *Bacillus butanolivorans*, but unexpectedly exhibit desirable high salt tolerance as well as low temperature growth and urease production. In another aspect, the present invention relates to compositions comprising at least one of such strains and an acceptable carrier. Such compositions are suitable for use in industrial, agricultural, aquacultural, environmental, wastewater treatment and/or probiotic applications.

BACKGROUND OF THE INVENTION

Because of their ability to synthesize multiple enzymes as well as their environmental acceptability, *Bacillus* species are employed in a multitude of commercial applications. These applications include cleaning products; drain cleaners; biological digesters; wastewater treatments; use in waste lagoons, grease traps, and plumbing systems; agricultural systems; and aquacultural systems; as well as activity in probiotic administrations. Due to the breadth of materials and environmental conditions which may be encountered in such uses, it is desirable to possess bacterial strains that produce multiple enzymes and which are capable of growth across a wide spectrum of environmental conditions.

Among the *Bacillus* species which are known to have commercial utility is *Bacillus simplex*. This species is known to produce proteases (which degrade proteins); lipases (which degrade lipids); esterases (which degrade esters) and amylases (which degrade starches). As is described by Heyrman et al. (2005, International Journal of Systematic and Evolutionary Microbiology 55: 119-131), *B. simplex* strains will grow at a range of useful temperatures (growth is observed at 20° C. and 30° C., but not at 45° C.); pH (strains grow "profusely" at pH 9 and pH 7; at pH 5 growth is "variable'); and will react with a broad variety of substrates. However, Heyrman et al. teaches that "no growth occurs in media supplemented with 7% NaCl" and that urease production is "negative". See Heyrman et al., cited above, page 129.

Such a lack of ability to grow at high salt concentrations has also been reported for other *B. simplex* strains. For example, Gomaa et al. (2007, Arab J. Biotech. 10(1): 107-116) disclose that a frozen sample of *Bacillus simplex* TWW-04 showed little growth at 5 mM NaCl while a 36 month subcultured sample exhibited no growth under such conditions.

*Bacillus butanolivorans* is closely related to *B. simplex* (having a 16S rRNA homology of 98.3% with *Bacillus simplex* DSM 1321) and was isolated from soil in Lithuania. *B. butanolivorans* is particularly effective to degrade n-butanol present in industrial waste streams. See Kuisiene et al. 2008, International Journal of Systematic and Evolutionary Microbiology 58: 505-509. However, like *B. simplex*, *B. butanolivorans* will not grow in high salt (e.g., 7% w/v) environments. See Kuisiene et al., cited above.

Accordingly, there is a need for *Bacillus* strains that grow in high salt environments and exhibit desirable enzymatic activity, including urease activity.

SUMMARY OF THE INVENTION

In one aspect the present invention relates to a biologically pure bacterial isolate having all the identifying characteristics of a bacterium selected from the group consisting of *Bacillus* strains ENV 734 (NRRL B-50800), ENV 735 (NRRL B-50801), ENV 736 (NRRL B-50802), and ENV 737 (NRRL B-50803).

In one embodiment, the biologically pure bacterial isolate is *Bacillus* strain ENV 734 (NRRL B-50800). In another embodiment, the biologically pure bacterial isolate is *Bacillus* strain ENV 735 (NRRL B-50801). In another embodiment, the biologically pure bacterial isolate is *Bacillus* strain ENV 736 (NRRL B-50802). In a further embodiment, the biologically pure bacterial isolate is *Bacillus* strain ENV 737 (NRRL B-50803).

The invention also provides a composition comprising any of the aforementioned bacterial isolates and an acceptable carrier. In certain embodiments, the carrier is an agriculturally acceptable carrier. In some embodiments, the carrier is suitable for probiotic administration. In further embodiments, the carrier is suitable for use in cleaning products, drain cleaners, biological digesters, wastewater treatments, or use in waste lagoons, grease traps, or plumbing systems.

In certain embodiments, the aforementioned composition comprises at least one additional bacteria or fungus. In some embodiments, the at least one additional bacteria is selected from the group consisting of *Bacillus* species, *Clostridium* species, *Pasteuria* species, *Pseudomonas* species, and *Actinomycetes*. In other embodiments, the at least one additional bacteria is selected from the group consisting of *Bacillus alcalophilus, Bacillus alvei, Bacillus amyloliquefaciens, Bacillus aneurinolyticus, Bacillus anthracis, Bacillus aquaemaris, Bacillus atrophaeus, Bacillus boronophilus, Bacillus brevis, Bacillus caldolyyicus, Bacillus centrosporus, Bacillus cereus, Bacillus circulan, Bacillus coagulans, Bacillus firmus, Bacillus flavothermus, Bacillus fusiformis, Bacillus globigii, Bacillus infernus, Bacillus larvae, Bacillus laterosporus, Bacillus lentus, Bacillus licheniformis, Bacillus megaterium, Bacillus mesentericus, Bacillus mucilaginosus, Bacillus mycoides, Bacillus natto, Bacillus pantothenicus, Bacillus papilliae, Bacillus polymyxa, Bacillus pseudoanthracis, Bacillus pumilus, Bacillus schlegelii, Bacillus simplex, Bacillus sphaericus, Bacillus sporothermodurans, Bacillus stearothermophilus, Bacillus subtilis, Bacillus thermoglucosidasius, Bacillus thuringiensis, Bacillus vulgatis, Bacillus weihenstephanensis, Bacillus macerans, Bacillus butanolivorans; Bradyrhizobium, Rhizobium; Clostridium thermocellum, Clostridium ljungdahlii, Clostridium acetobutylicum, Clostridium. beijerinckii, Clostridium butyricum; Pasteuria penetrans, Pasteuria usagae, Pasteuria. nishizawae, Pasteuria reniformis; Pseudomonas fluorescens, Pseudomonas putida, Pseudomonas chlororaphis, Pseudomonas syringae; Streptomyces griseofulvin, Streptomyces griseoviridis, Streptomyces sindeneusis, and Saccharopolyspora spinosa*; and the at least one additional fungus is selected from the group consisting of *Metarhizium anisopliae, Beauveria bassiana, Paecilomy-* ces lilacinus, Trichoderma reesei, Phanerochaete chrysosporium, and Penicillium bilaii, or is from a genus selected from the group consisting of Glomus, Acaulospora, Entrophosphora, Gigaspora, Scutellospora and Scierocytis.

The invention also provides a method for preparing a composition comprising any of the aforementioned bacterial isolates, the method comprising mixing the isolate with an acceptable carrier to form a composition.

In other embodiments, the invention provides a method for enhancing the growth of a plant propagative material comprising coating a plant propagative material with a composition comprising any of the aforementioned bacterial isolates, wherein growth of the plant propagative material is enhanced relative to a corresponding control plant propagative material that is not coated with the bacterial isolate.

The invention also provides a method for treating wastewater comprising adding a composition comprising any of the aforementioned bacterial isolates to wastewater.

In a further embodiment, the invention provides a method for environmental remediation comprising applying any of the aforementioned bacterial isolates to soil or water.

In another embodiment, the invention provides a method for treating water in an aquaculture system, comprising contacting any of the aforementioned bacterial isolates with water in an aquaculture system.

DETAILED DESCRIPTION OF THE INVENTION

In one aspect the present invention relates to a biologically pure bacterial isolate having all the identifying characteristics of a bacterium selected from the group consisting of Bacillus strains ENV 734 (NRRL B-50800), ENV 735 (NRRL B-50801), ENV 736 (NRRL B-50802), and ENV 737 (NRRL B-50803).

ENV 734, ENV 735, ENV 736 and ENV 737 were isolated from stream water in Pennsylvania, in the United States of America. Samples of these strains were deposited in the collection of the Agricultural Research Service Culture Collection (NRRL), 1815 N. University St., Peoria, Ill., 61604, USA on Jan. 22, 2013 and have been designated the following accession numbers:

| Strain | Accession Number |
| --- | --- |
| ENV 734 | NRRL B-50800 |
| ENV 735 | NRRL B-50801 |
| ENV 736 | NRRL B-50802 |
| ENV 737 | NRRL B-50803 |

Samples of each isolate were analyzed by sequencing the 16S rRNA gene in order to establish taxonomy. It was found, based upon the consensus sequences tested, that all four strains possessed a sequence homology of greater than 99% with Bacillus simplex; and a DNA sequence homology of greater than 99.9% with Bacillus butanolivorans.

Propagation of the bacterial strains of this invention may be effected by culture under any conventional conditions and in media which promote their growth. A variety of known culture media such as tryptic soy broth are suitable for use for the production of the strains of the invention. As a practical matter, and without being limited thereto, the bacteria are typically grown in aerobic liquid cultures on media which contain sources of carbon, nitrogen, and inorganic salts assimilable by the microorganism and supportive of efficient cell growth. Preferred carbon sources are hexoses such as glucose, but other assimilable sources include glycerol, amino acids, xylose, etc. Many inorganic and proteinaceous materials may be used as nitrogen sources in the growth process. Preferred nitrogen sources are amino acids and urea, but others include gaseous ammonia, inorganic salts of nitrate and ammonium, vitamins, purines, pyrimidines, yeast extract, beef extract, proteose peptone, soybean meal, hydrolysates of casein, distiller's solubles, and the like. Among the inorganic minerals that can be incorporated into the nutrient medium are the customary salts capable of yielding calcium, zinc, iron, manganese, magnesium, copper, cobalt, potassium, sodium, molybdate, phosphate, sulfate, chloride, borate, and like ions. Similarly, suitable pH and temperature conditions are also variable, and optimal conditions will vary with the particular strain.

In certain embodiments, the identifying characteristics of the aforementioned biologically pure bacterial isolates comprise urease activity, lipase activity, protease activity, amylase activity, carboxymethylcellulase (CMC) activity, growth at 4° C., no growth at 45° C., growth at pH 5.5, growth at pH 9.0, growth at 7% (w/v) NaCl, and antifungal activity. In some embodiments, the one or more identifying characteristics comprise urease activity, lipase activity, growth at 4° C., no growth at 45° C., growth at pH 5.5, growth at pH 9.0, growth at 7% (w/v) NaCl, and antifungal activity. In other embodiments, the one or more identifying characteristics comprise urease activity, growth at 4° C., and growth in medium comprising at least 7% (w/v) NaCl. In a preferred embodiment, the one or more identifying characteristics comprise urease activity, growth at 4° C., growth in medium comprising at least 7% (w/v) NaCl, and growth at pH 5.5. In another preferred embodiment, the one or more identifying characteristics comprise urease activity. In yet another preferred embodiment, the one or more identifying characteristics comprise growth at 4° C. In a further preferred embodiment, the one or more identifying characteristics comprise growth at 7% (w/v) NaCl.

In a preferred embodiment of the aforementioned biologically pure bacterial isolates, the antifungal activity comprises inhibiting the growth of a fungus selected from the group consisting of Rhizoctonia solani, Pythium aphanidermatum, Pythium irregulare, Phytophthora parasitica, and Fusarium oxysporum.

In some embodiments, the aforementioned biologically pure bacterial isolates are capable of growth at temperatures from 4° C. to 37° C. In a further embodiment, the bacterial isolates are incapable of growth at temperatures of 45° C. and above. In a still further embodiment the bacterial isolates are capable of growth throughout the pH range of 5.5 to 9.0. In a further embodiment, the bacterial isolates are capable of growth at NaCl concentrations up to and including 7% (w/v) NaCl. In a preferred embodiment, the bacterial isolates are capable of growth at temperatures from 4° C. to 37° C., incapable of growth at temperatures of 45° C. and above, capable of growth throughout the pH range of 5.5 to 9.0, and capable of growth at NaCl concentrations up to and including 7% (w/v) NaCl.

The compositions of this invention may comprise at least one of ENV 734 (NRRL B-50800), ENV 735 (NRRL B-50801), ENV 736 (NRRL B-50802), and ENV 737 (NRRL B-50803); and an acceptable carrier. As is employed herein, the term "acceptable carrier" refers to a carrier which is typically employed in the field involved (for example a carrier typically employed in industrial, agricultural, aquacultural, environmental and/or probiotic applications) which does not adversely affect the bacterial strain involved. Such carriers are well known to those of ordinary skill in the art.

In a preferred embodiment, the carrier is an agriculturally acceptable carrier. In another preferred embodiment, the carrier is an aquaculturally acceptable carrier. In a further preferred embodiment, the carrier is suitable for environmental administration. In yet another preferred embodiment, the carrier is suitable for probiotic administration. For many industrial and/or agricultural applications, carriers include porous solid carriers such as talc, bentonite, clay, kaolin, diatomaceous earth, white carbon, vermiculite, slaked lime, siliceous sand, ammonium sulfate, and the like; as well as liquid carriers such as water, isopropyl alcohol, xylene, cyclohexanone, methylnaphthalene, and alkyl glycol and the like. For probiotic use, pharmaceutically carriers such as sugars and starches which are typically employed may be utilized.

The compositions may comprise those amounts of carrier and *Bacillus* typically employed in the pertinent application, which amounts are well known and/or easily determinable.

The compositions of this invention may further comprise one or more additional bacterial or fungal strains in order to increase their efficacy and/or range of action. In general, any useful bacterial or fungal organism may be included. Illustrative of such bacteria are *Bacillus* species such as *B. alcalophilus, B. alvei, B. amyloliquefaciens, B. aneurinolyticus, B. anthracis, B. aquaemaris, B. atrophaeus, B. boronophilus, B. brevis, B. caldolyyicus, B. centrosporus, B. cereus, B. circulan, B. coagulans, B. firmus, B. flavothermus, B. fusiformis, B. globigii, B. infernus, B larvae, B. laterosporus, B. lentus, B. licheniformis, B. megaterium, B. mesentericus, B. mucilaginosus, B. mycoides, B. natto, B. pantothenicus, B. papilliae, B. polymyxa, B. pseudoanthracis, B. pumilus, B. schlegelii, B. simplex, B. sphaericus, B. sporothermodurans, B. stearothermophilus, B. subtilis, B. thermoglucosidasius, B. thuringiensis, B. vulgatis, B. weihenstephanensis, B. macerans,* and *B. butanolivorans; Bradyrhizobium* and *Rhizobium; Clostridium* species such as *C. thermocellum, C. ljungdahlii, C. acetobutylicum, C. beijerinckii,* and *C. butyricum; Pasteuria* species such as *P. penetrans, P. usagae, P. nishizawae,* and *P. reniformis; Pseudomonas* species, such as *P. fluorescens, P. putida, P. chlororaphis,* and *P. syringae; Actinomycetes,* such as *Streptomyces griseofulvin, Streptomyces griseoviridis, Streptomyces sindeneusis,* and *Saccharopolyspora spinosa,* as well as genetically modified variants of any of the aforementioned bacterial species. Fungi that may be used in the compositions include, but are not limited to, *Metarhizium anisopliae, Beauveria bassiana, Paecilomyces lilacinus, Trichoderma reesei, Phanerochaete chrysosporium, Penicillium bilaii*; strains of mycorrhiza selected from genera *Glomus, Acaulospora, Entrophosphora, Gigaspora, Scutellospora* and *Scierocytis,* as well as genetically modified variants of such fungi.

The invention also provides a method for preparing the aforementioned compositions comprising mixing the aforementioned biologically pure bacterial isolates with an acceptable carrier. In certain embodiments, the composition is a dried mixture and may be produced by processes such as spray-drying, freeze-drying, air drying or drum drying. In other embodiments, the composition is a liquid formulation.

The invention also provides a method for enhancing the growth of a plant propagative material comprising coating a plant propagative material with a composition comprising the aforementioned biologically pure bacterial isolates, wherein growth of the plant propagative material is enhanced relative to a corresponding control plant propagative material that is not coated with the bacterial isolate.

As is employed herein, the term "plant propagative material" is intended to include all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring. Preferably, the term plant propagative material denotes seeds.

Enhanced growth includes, but is not limited to, increases in one or more of the following parameters: percent germination, speed of germination, percent emergence, seedling biomass, seedling height, root length, root biomass, shoot biomass, flower number, flower size, yield, and seed yield.

Plants that are particularly useful in the present invention include monocotyledonous and dicotyledonous plants including but not limited to fodder or forage legumes, ornamental plants, food crops, trees, or shrubs selected from *Acer* spp., *Allium* spp., *Amaranthus* spp., *Ananas comosus, Apium graveolens, Arachis* spp, *Asparagus officinalis, Beta vulgaris, Brassica* spp. (e.g. *Brassica napus, Brassica rapa* ssp. [canola, oilseed rape, turnip rape]), *Camellia sinensis, Canna indica, Cannabis sativa, Capsicum* spp., *Castanea* spp., *Cichorium endivia, Citrullus lanatus,* Citrus spp., *Cocos* spp., *Coffea* spp., *Coriandrum sativum, Corylus* spp., *Crataegus* spp., *Cucurbita* spp., *Cucumis* spp., *Daucus carota, Fagus* spp., *Ficus carica, Fragaria* spp., *Ginkgo biloba, Glycine* spp. (e.g. *Glycine max, Soja hispida* or *Soja max), Gossypium hirsutum, Helianthus* spp. (e.g. *Helianthus annuus), Hibiscus* spp., *Hordeum* spp. (e.g. *Hordeum vulgare), Ipomoea batatas, Juglans* spp., *Lactuca sativa, Linum usitatissimum, Litchi chinensis, Lotus* spp., *Luffa acutangula, Lupinus* spp., *Lycopersicon* spp. (e.g. *Lycopersicon esculenturn, Lycopersicon lycopersicum, Lycopersicon pyriforme), Malus* spp., *Medicago sativa, Mentha* spp., *Miscanthus sinensis, Morus nigra, Musa* spp., *Nicotiana* spp., *Olea* spp., *Oryza* spp. (e.g. *Oryza sativa, Oryza latifolia), Panicum miliaceum, Panicum virgatum, Passiflora edulis, Petroselinum crispum, Phaseolus* spp., *Pinus* spp., *Pistacia vera, Pisum* spp., *Poa* spp., *Populus* spp., *Prunus* spp., *Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum), Sorghum bicolor, Sorghum halepense, Spinacia* spp., *Tamarindus indica, Theobroma cacao, Trifolium* spp., *Triticosecale rimpaui, Triticum* spp. (e.g. *Triticum aestivum, Triticum durum, Triticum turgidum, Triticum hybernum, Triticum macha, Triticum sativum* or *Triticum vulgare), Vaccinium* spp., *Vicia* spp., *Vigna* spp., *Viola odorata, Vitis* spp., and *Zea mays.* Especially preferred are rice, oilseed rape, canola, soybean, corn (maize), cotton, sugarcane, alfalfa, *sorghum,* and wheat.

In certain embodiments, the plant propagative material is coated with the biologically pure bacterial isolate by any conventional means typically employed to coat seed or other germinative material, provided that such means does not adversely affect the viability of the bacteria. Conventional means which may be employed include spray treatment, drip treatment, drench treatment, painting treatment, film-coat treatment, pellet-coat treatment and the like. Methods of seed coating are known in the art and are described, for example, in U.S. Pat. No. 7,989,391 and U.S. Pat. No. 5,849,320.

In addition to biologically active ingredients, seed coating compositions may include any materials and additives that are either part of the formulations of the active ingredient or contribute to the handling qualities of the seed coating or its functionality and durability on the seed. An example of a coating additive is a coating polymer which binds the active ingredients to the seed. Seed-coating polymers may include, but are not limited to, proteins, polysaccharides, polyesters, polyurethanes, polymers prepared from unsaturated monomers, and combinations thereof.

Other additives contributing to the handling qualities of the seed coating or its functionality and durability on the seed include but are not limited to surfactants, sequestering agents, plasticizers, colorants and dyes, brighteners, emulsifiers, flow agents, coalescing agents, defoaming agents, thickeners, waxes, bactericides, fillers, polymers, wetting agents and anti-freezing agents. The nature and action of such additives are well-known to those skilled in the art of formulation. Additives should not interfere with the action of the bacterium.

Binders that are useful in the present invention preferably comprise an adhesive polymer that may be natural or synthetic and is without phytotoxic effect on the seed to be coated. The binder may be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; fats; oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

The amount of binder in the coating can vary, but will be in the range of about 0.01 to about 25% of the weight of the seed, more preferably from about 0.05 to about 15%, and even more preferably from about 0.1% to about 10%.

The propagative material coating may optionally include a filler. The filler can be an absorbent or an inert filler, such as are known in the art, and may include woodflours, clays, activated carbon, sugars, diatomaceous earth, cereal flours, fine-grain inorganic solids, calcium carbonate, and the like. Clays and inorganic solids, which may be used, include calcium bentonite, kaolin, china clay, talc, perlite, mica, vermiculite, silicas, quartz powder, montmorillonite and mixtures thereof. Sugars, which may be useful, include dextrin and maltodextrin. Cereal flours include wheat flour, oat flour and barley flour.

The filler is selected so that it will provide a proper microclimate for the seed, for example the filler is used to increase the loading rate of the active ingredients and to adjust the control-release of the active ingredients. The filler can aid in the production or process of coating the seed. The amount of filler can vary, but generally the weight of the filler components will be in the range of about 0.05 to about 75% of the seed weight, more preferably about 0.1 to about 50%, and even more preferably about 0.5% to 15%.

Optionally, a plasticizer can be used in the coating formulation. Plasticizers are typically used to make the film that is formed by the coating layer more flexible, to improve adhesion and spreadability, and to improve the speed of processing. Improved film flexibility is important to minimize chipping, breakage or flaking during storage, handling or sowing processes. Many plasticizers may be used, however, useful plasticizers include polyethylene glycol, glycerol, butylbenzylphthalate, glycol benzoates and related compounds. The range of plasticizer in the coating layer will be in the range of from about 0.1 to about 20% by weight.

The treated seeds may also be enveloped with a film overcoating to protect the active components coating. Such overcoatings are known in the art and may be applied using conventional fluidized bed and drum film coating techniques.

The plant propagative material may also be treated with the composition comprising the biologically pure bacterial isolate by applying the composition to the plant growth medium before or after planting. For example, the composition may be applied to the soil by spraying or through an irrigation system. The composition may also be applied to the plant growth medium in a solid form, for example as a dried powder.

The invention also provides a method for treating wastewater comprising adding a composition comprising the aforementioned biologically pure bacterial isolates to wastewater. The compositions may be used for the treatment of any wastewater including municipal, industrial or agricultural wastewater, lift stations, pulp and paper wastewater, food processing wastewater, petrochemical wastewater and animal waste wastewater. The compositions may also be used for onsite wastewater treatment in septic tanks, grease traps and holding tanks. In certain embodiments, the compositions may be used to degrade fats, oils and grease in waste water generated by restaurants and commercial kitchens. The compositions may also be added to small-scale wastewater holding tanks for breaking down waste in boats, portable toilets and other small waste holding systems.

The wastewater treatment methods of the invention may also be conducted in a variety of reactor systems. For example, while the wastewater treatment will typically be conducted in a tank, the reaction may be conducted in any vessel or reservoir used for wastewater storage provided that suitable conditions are provided to maintain a suitable environment to support the growth and biological activity of the bacteria in the composition. Suitable wastewater treatment reactor systems include but are not limited to suspended-growth bioreactors and attached-growth bioreactors. In suspended-growth bioreactors, the composition may be mixed with the wastewater by the agitation of the liquid. In an attached-growth bioreactor, various sold support media are provided to allow the bacteria in the composition to attach to the surface thereof. Suitable media include, but are not limited to trickling filters, rotating biological contactors, packed-bed reactors, and others known in the art. Yet another attached-growth bioreactor that is suitable for use herein is a fluidized or moving bed reactor. In this system, bio-carriers containing the bacteria remain suspended in the wastewater being treated, fluidized by the drag forces associated with the mixing of the water. The bacteria may be entrapped in polymeric porous materials such as particles of polyvinyl alcohol (PVA), polyethylene glycol (PEG), or other polymer gels such as calcium alginate. The bacteria may be attached forming biofilms in suspended carriers such as K1, K3, MiniChip, and BiofilmChip plastic carriers (AnoxKaldnes, Sweden). Fluidized bed reactors allow the populations of microorganisms to increase rapidly, thus reducing the time necessary for wastewater treatment. Methods of wastewater treatment using bacterial strains are known in the art and are described, for example, in U.S. Patent Application Publication Nos. 2012/0000849 and 2011/0180476.

The invention also provides methods of environmental remediation comprising applying any of the aforementioned bacterial isolates to soil or water. *Bacillus* species may be used for environmental remediation both in water and land. The mode of action for soil remediation is much the same as described above for wastewater treatment. The bacteria break down chemicals and pollutants via enzyme and acid generation that further break down the pollutant or bind it in a more non-reactive form.

The invention also provides methods for treating water in an aquaculture system, comprising contacting any of the aforementioned bacterial isolates with water in an aquaculture system. The bacterial isolates may be added directly to the water, or may be used in a biofilter system as described, for example, in U.S. Pat. No. 7,082,893. The bacterial isolates may be used in an aquaculture system to remediate and break down the waste generated by aquatic species raised for food such as shrimp and fish. The bacterial isolates may also be utilized in aquaculture to cycle nutrients, break down lipids, proteins, starches as well as produce amino acids & enzymes which enhance feed conversion. The bacterial isolates may also be used to generate natural antibiotics and provide competitive exclusion to protect against pathogens in the environment as well as the animal's gastrointestinal tract. This generation of natural antibiotics and competitive exclusion against pathogens may also be utilized in human probiotics or direct fed microbials for production animals and companion animals.

EXAMPLES

The following examples are intended to further illustrate the invention, but are not intended to limit the invention in any manner whatsoever.

Example 1—Growth at Different Temperatures

Samples of ENV 734, ENV 735, ENV 736 and ENV 737 were evaluated for their growth at different temperatures by streaking cultures on Plate Count Agar (PCA) plates. The plates were pre-incubated at the temperatures tested. *Bacillus simplex* strain DSM 1321 was obtained from the DSMZ collection and tested as a control. The results of such testing are summarized in Table 1 below:

TABLE 1

| Strain | +4° C. | 30° C. | 37° C. | 45° C. |
|---|---|---|---|---|
| ENV 734 | + | + | + | − |
| ENV 735 | + | + | + | − |
| ENV 736 | + | + | + | − |
| ENV 737 | + | + | + | − |
| B. simplex | + | + | + | − |

These results show that ENV 734, ENV 735, ENV 736 and ENV 737 grow at low temperatures of 4° C. but do not grow at elevated temperatures of 45° C. *Bacillus simplex* strain DSM 1231 showed a similar temperature growth pattern.

Example 2—Enzymatic Activity

Samples of ENV 734, ENV 735, ENV 736 and ENV 737 were evaluated for their production of urease, lipase, protease, amylase and carboxymethylcellulase ("CMC"). Petri dishes containing agar, the specific substrate tested for digestion, and the appropriate amount of inorganic nitrogen and micronutrients were aseptically prepared. For example, milk was the substrate for the protease assay, urea was the substrate for the urease assay, Difco lipase reagent (Reference #215355) was the substrate for the lipase assay, corn starch was the substrate for the amylase assay, and carboxymethylcellulose was the substrate for the CMCase assay. After the plates were prepared, each strain of bacteria was grown individually, overnight, in Tryptic Soy Broth and used to inoculate the enzyme test plates. Each plate was inoculated once in each of four quadrants with a small amount of the overnight culture. A positive and negative control strain of bacteria was included to insure the assay was performing properly. The inoculated plates were incubated at 30° C. for 48 hours and observed for a clearing zone or color change around the colony. The size of the clearing zone or color change halo around the colony was compared to that of the control and recorded. *Bacillus simplex* strain DSM 1321 was obtained from the DSMZ collection and tested as a control. The results of such testing are summarized in Table 2 below:

TABLE 2

Enzymatic activity of various strains. "+" indicates that the bacterial strain exhibited activity for the designated enzyme, "−" indicates that the bacterial isolate exhibited no activity for the designated enzyme.

| Strain | Urease | Lipase | Protease | Amylase | CMC |
|---|---|---|---|---|---|
| ENV 734 | + | + | + | + | + |
| ENV 735 | + | + | + | + | + |
| ENV 736 | + | + | + | + | + |
| ENV 737 | + | + | + | + | + |
| B. simplex | − | + | + | + | + |

Strains ENV 734, ENV 735, ENV 736 and ENV 737 exhibited high levels of urease activity, while the *Bacillus simplex* control exhibited no urease activity.

Example 3—Comparison of ENV 734, ENV 735, ENV 736 and ENV 737 with *B. simplex* and *B. butanolivorans* for Growth Characteristics and Urease Activity The following biological characteristics of ENV 734, ENV 735, ENV 736 and ENV 737 were evaluated in comparison with *Bacillus simplex* strain DSM 1321. Test tubes containing Tryptic Soy Broth with the pH adjusted to 5.5, 7.0, and 9.0 were prepared and autoclaved. Tubes at pH 7.0 with the addition of 7% sodium chloride were also prepared. Two tubes for each test parameter were inoculated with 10 microliters of an overnight culture of an individual strain to be tested. This was repeated for all strains to be tested, and positive and negative control strains were included to insure the assays were working properly. The pH 5.5, pH 9.0, and pH 7.0 with 7% sodium chloride tubes that were inoculated were incubated at 30° C. and the pH 7.0 tubes were incubated at 45° C. After 48 hours of incubation the tubes were removed and checked for growth by visual evaluation of turbidity of the culture, and growth was recorded as positive or negative. Each tube showing positive growth was streaked on a fresh Tryptic Soy Agar plate to verify the correct strain was growing in the tube based on colony morphology. The reported results for *Bacillus butanolivorans* (Kusiene et al., cited above) are also presented in Table 3:

TABLE 3

|  | ENV 734 | ENV 735 | ENV 736 | ENV 737 | Bacillus simplex | Bacillus butanolivorans |
|---|---|---|---|---|---|---|
| Growth at 45° C. | − | − | − | − | − | + |
| Growth at pH 5.5 | + | + | + | + | − | Not Tested |
| Growth at pH 9.0 | + | + | + | + | + | − |
| Urease Production | + | + | + | + | − | Not Tested |
| Growth at 7% (w/v) NaCl | + | + | + | + | − | − |

The above results show that, despite the high degree of homology between the strains of this invention and both *B. simplex* and *B. butanolivorans*, strains ENV 734, ENV 735, ENV 736 and ENV 737 exhibit unexpected differences in several of their attributes—most notably the ability to grow in high salt environments.

Example 4—Antifungal Activity

Antifungal activity was tested by spotting bacteria on PCA plates and incubating plates at 30° C. for 2, 4 or 7 days, then putting a piece of fungus culture on these plates and observing the bacteria's ability to interfere with fungus growth. The fungi tested were *Rhizoctonia solani*, *Pythium aphanidermatum* ("*P. aphan.*"), *Pythium irregulare*, *Phytophthora parasitica* and *Fusarium oxysporum*. The results of such testing are summarized in Table 4 below:

TABLE 4

| Strain | ENV 734 | ENV 735 | ENV 736 | ENV 737 |
|---|---|---|---|---|
| *R. solani* | | | | |
| 2 Days | + | ++ | ++ | +− |
| 4 Days | +++ | +++ | +++ | ++ |
| *P. aphan.* | | | | |
| 2 Days | − | − | − | − |
| 4 Days | ++ | +++ | +++ | + |
| 7 Days | +++ | +++ | +++ | +++ |
| *P. irregulare* | | | | |
| 2 Days | + | ++ | ++ | + |
| 4 Days | +++ | +++ | +++ | ++ |
| 7 Days | +++ | +++ | ++++ | +++ |
| *P. parasitica* | | | | |
| 2 Days | ++ | +++ | +++ | ++ |
| 4 Days | +++ | +++ | +++ | +++ |
| *F. oxysporum* | | | | |
| 2 Days | + | ++ | ++ | + |
| 4 Days | ++ | +++− | +++− | ++ |

In Table 4 above:
+++ Best antifungal activity—very little or no fungus growth
+++− Antifungal activity less than +++, but more than ++
++ Less antifungal actvity—about half plate covered with fungus
+ Little antifungal activity—most plate covered with fungus
+− Antifungal activity less than + but more than −
− No antifungal activity—plate is covered with fungus The above results demonstrate that ENV 734, ENV 735, ENV 736 and ENV 737 exhibit desirable antifungal activity.

Example 5—Evaluation of Plant Growth for Maize Seeds Coated with Compositions Comprising ENV 734, ENV 735, ENV 736 or ENV 737

Maize seeds are coated with compositions comprising ENV 734, ENV 735, ENV 736, or ENV 737 and an agriculturally acceptable carrier. Maize seed coated with the agriculturally acceptable carrier without the bacteria are used as a control. Seed coating is performed by conventional means. Seed germination rates are measured in greenhouse and field trials by measuring seedling emergence at regular intervals beginning on the first day that plants emerge and continuing for three weeks after the first date of emergence. Seedling growth rates are also determined by measuring seedling height, fresh weight, and dry weight at regular intervals beginning one week after the first date of emergence.

What is claimed is:

1. A method for enhancing the growth of a plant propagative material comprising coating a plant propagative material with a composition comprising a biologically pure bacterial isolate in an amount effective to enhance the growth of the plant propagative material relative to a plant propagative material that is not coated with the composition, wherein the biologically pure bacterial isolate has all the identifying characteristics of a bacterium selected from the group consisting of *Bacillus* strains ENV 734 (NRRL B-50800), ENV 735 (NRRL B-50801), ENV 736 (NRRL B-50802), and ENV 737 (NRRL B-50803), and wherein the identifying characteristics comprise urease activity, lipase activity, protease activity, amylase activity, carboxymethylcellulase (CMC) activity, growth at 4° C., no growth at 45° C., growth at pH 5.5, growth at pH 9.0, growth at 7% (w/v) NaCl, and antifungal activity.

2. The method of claim 1, wherein the biologically pure bacterial isolate is *Bacillus* strain ENV 734 (NRRL B-50800).

3. The method of claim 1, wherein the biologically pure bacterial isolate is *Bacillus* strain ENV 735 (NRRL B-50801).

4. The method of claim 1, wherein the biologically pure bacterial isolate is *Bacillus* strain ENV 736 (NRRL B-50802).

5. The method of claim 1, wherein the biologically pure bacterial isolate is *Bacillus* strain ENV 737 (NRRL B-50803).

6. The method of claim 1, wherein the composition further comprises an agriculturally acceptable carrier.

7. The method of claim 1, wherein the composition further comprises at least one additional bacterium or fungus.

8. The method of claim 7, wherein the at least one additional bacterium is selected from the group consisting of *Bacillus* species, *Clostridium* species, *Pasteuria* species, *Pseudomonas* species, and *Actinomycetes*.

9. The method of claim 7, wherein the at least one additional bacterium is selected from the group consisting of *Bacillus alcalophilus*, *Bacillus alvei*, *Bacillus amyloliquefaciens*, *Bacillus aneurinolyticus*, *Bacillus anthracis*, *Bacillus aquaemaris*, *Bacillus atrophaeus*, *Bacillus boronophilus*, *Bacillus brevis*, *Bacillus caldolyyicus*, *Bacillus centrosporus*, *Bacillus cereus*, *Bacillus circulan*, *Bacillus coagulans*, *Bacillus firmus*, *Bacillus flavothermus*, *Bacillus fusiformis*, *Bacillus globigii*, *Bacillus infernus*, *Bacillus larvae*, *Bacillus laterosporus*, *Bacillus lentus*, *Bacillus licheniformis*, *Bacillus megaterium*, *Bacillus mesentericus*, *Bacillus mucilaginosus*, *Bacillus mycoides*, *Bacillus natto*, *Bacillus pantothenicus*, *Bacillus papilliae*, *Bacillus polymyxa*, *Bacillus*

*pseudoanthracis, Bacillus pumilus, Bacillus schlegelii, Bacillus simplex, Bacillus sphaericus, Bacillus sporothermodurans, Bacillus stearothermophilus, Bacillus subtilis, Bacillus thermoglucosidasius, Bacillus thuringiensis, Bacillus vulgatis, Bacillus weihenstephanensis, Bacillus macerans, Bacillus butanolivorans; Bradyrhizobium, Rhizobium; Clostridium thermocellum, Clostridium ljungdahlii, Clostridium acetobutylicum, Clostridium beijerinckii, Clostridium butyricum; Pasteuria penetrans, Pasteuria usagae, Pasteuria nishizawae, Pasteuria reniformis; Pseudomonas fluorescens, Pseudomonas putida, Pseudomonas chlororaphis, Pseudomonas syringae; Streptomyces griseofulvin, Streptomyces griseoviridis, Streptomyces sindeneusis,* and *Saccharopolyspora spinosa;* and the at least one additional fungus is selected from the group consisting of *Metarhizium anisopliae, Beauveria bassiana, Paecilomyces lilacinus, Trichoderma reesei, Phanerochaete chrysosporium,* and *Penicillium bilaii,* or is from a genus selected from the group consisting of *Glomus, Acaulospora, Entrophosphora, Gigaspora, Scutellospora* and *Scierocytis.*

10. The method of claim 1, further comprising preparing the composition by mixing the biologically pure bacterial isolate with an acceptable carrier.

11. A method for enhancing the growth of a plant propagative material comprising applying to a plant growth medium of a composition comprising a biologically pure bacterial isolate in an amount effective to enhance the growth of the plant propagative material relative to a plant propagative material in a plant growth medium that is not treated with the biologically pure isolate has all the identifying characteristics of a bacterium selected from the group consisting of *Bacillus* strains ENV 734 (NRRL B-50800), ENV 735 (NRRL B-50801), ENV 736 (NRRL B-50802), and ENV 737 (NRRL B-50803), wherein the identifying characteristics comprise urease activity, lipase activity, protease activity, amylase activity, carboxymethylcellulase (CMC) activity, growth at 4° C., no growth at 45° C., growth at pH 5.5, growth at pH 9.0, growth at 7% (w/v) NaCl, and antifungal activity, and wherein the plant propagative material is contacted with the plant growth medium before or after the composition is applied to the plant growth medium.

12. The method of claim 11, wherein the biologically pure bacterial isolate is *Bacillus* strain ENV 734 (NRRL B-50800).

13. The method of claim 11, wherein the biologically pure bacterial isolate is *Bacillus* strain ENV 735 (NRRL B-50801).

14. The method of claim 11, wherein the biologically pure bacterial isolate is *Bacillus* strain ENV 736 (NRRL B-50802).

15. The method of claim 11, wherein the biologically pure bacterial isolate is *Bacillus* strain ENV 737 (NRRL B-50803).

16. The method of claim 11, wherein the composition further comprises an agriculturally acceptable carrier.

17. The method of claim 11, wherein the composition further comprises at least one additional bacterium or fungus.

18. The method of claim 17, wherein the at least one additional bacterium is selected from the group consisting of *Bacillus* species, *Clostridium* species, *Pasteuria* species, *Pseudomonas* species, and *Actinomycetes.*

19. The method of claim 17, wherein the at least one additional bacterium is selected from the group consisting of *Bacillus alcalophilus, Bacillus alvei, Bacillus amyloliquefaciens, Bacillus aneurinolyticus, Bacillus anthracis, Bacillus aquaemaris, Bacillus atrophaeus, Bacillus boronophilus, Bacillus brevis, Bacillus caldolyyicus, Bacillus centrosporus, Bacillus cereus, Bacillus circulan, Bacillus coagulans, Bacillus firmus, Bacillus flavothermus, Bacillus fusiformis, Bacillus globigii, Bacillus infernus, Bacillus larvae, Bacillus laterosporus, Bacillus lentus, Bacillus licheniformis, Bacillus megaterium, Bacillus mesentericus, Bacillus mucilaginosus, Bacillus mycoides, Bacillus natto, Bacillus pantothenicus, Bacillus papilliae, Bacillus polymyxa, Bacillus pseudoanthracis, Bacillus pumilus, Bacillus schlegelii, Bacillus simplex, Bacillus sphaericus, Bacillus sporothermodurans, Bacillus stearothermophilus, Bacillus subtilis, Bacillus thermoglucosidasius, Bacillus thuringiensis, Bacillus vulgatis, Bacillus weihenstephanensis, Bacillus macerans, Bacillus* butanolivorans; *Bradyrhizobium, Rhizobium; Clostridium thermocellum, Clostridium ljungdahlii, Clostridium acetobutylicum, Clostridium beijerinckii, Clostridium butyricum; Pasteuria penetrans, Pasteuria usagae, Pasteuria nishizawae, Pasteuria reniformis; Pseudomonas fluorescens, Pseudomonas putida, Pseudomonas chlororaphis, Pseudomonas syringae; Streptomyces griseofulvin, Streptomyces griseoviridis, Streptomyces sindeneusis,* and *Saccharopolyspora spinosa;* and the at least one additional fungus is selected from the group consisting of *Metarhizium anisopliae, Beauveria bassiana, Paecilomyces lilacinus, Trichoderma reesei, Phanerochaete chrysosporium,* and *Penicillium bilaii,* or is from a genus selected from the group consisting of *Glomus, Acaulospora, Entrophosphora, Gigaspora, Scutellospora* and *Scierocytis.*

20. The method of claim 11, further comprising preparing the composition by mixing the biologically pure bacterial isolate with an acceptable carrier.

\* \* \* \* \*